United States Patent [19]

Kit

[11] 4,307,189

[45] Dec. 22, 1981

[54] METHOD FOR THE QUANTITATIVE DETERMINATION OF TERMINAL DEOXYNUCLEOTIDYL TRANSFERASE IN BIOLOGICAL SAMPLES

[76] Inventor: Malon Kit, 11935 Wink Dr., Houston, Tex. 77024

[21] Appl. No.: 132,670

[22] Filed: Mar. 21, 1980

[51] Int. Cl.$^3$ .................... C12Q 1/68; C12Q 1/48; C12Q 1/29; C12Q 1/00
[52] U.S. Cl. .................................... 435/6; 435/4; 435/15; 435/29; 424/1; 424/7; 23/230 B
[58] Field of Search ............... 435/4, 6, 15, 29, 172, 435/193, 194; 424/1, 1.5, 2, 7; 23/230 B

[56] References Cited

PUBLICATIONS

Tsou. et al., "Synthesis of 1,N$^6$-ethens-2-AZA-adenosine(2-AZA-(-adensine); A New Cytotoxic Fluorescent Nucleoside", Nuclear Acids Res. vol. 1, No. 4 (1974) pp. 531–547.
Hoard et al., "Conversion of Mono-and Olryodeoxyribonucleotides to 5'-Triphosphates", J. Am. Chem. Soc. vol. 87, No. 8 (1965), pp. 1785–1788.
Bhalla et al., "Selective Inhibition of Terminal Deoxynucleotidyl Transferase (TdT) by Adenosine Ribonucleoside Triphosphate and its Application in the Detection of TdT in Human Leukemia", Biochem. Biophys. Res. Comm. vol. 76, No. 4 (1977) pp. 1056–1061.
Dicioccio et al., "Structure-Activity Relationships and Kinetic Analyses of Polyribonucleotide Inhibition of Human Cellulur Deoxynucleotide-Polymerizing Enzymes", Biochem. Biophys. Acta, vol. 478, (1977), pp. 274–285.
Coleman et al., "Serial Observations on Terminal Deoxynucleotidyl Transferase Activity and Lymphoblast Surface Markers in Acute Lymphoblastic Leukemia", Can. Res., vol. 36, (1976), pp. 120–127.
Mertelsmann et al., "Improved Biochemical Assay for Terminal Deoxynucleotidyl Transferase in Human Blood Cells Results in 89 Adult Patients with Lymphoid Leukemias and Malignant Lymphomas in Leukemic Phase", Leuk. Res. vol. 2, No. 1, (1978), pp. 57–69.
Sattsangi et al., "1,N$^2$-Ethenoguanine and N$^2$,3 Ethenoguanine Synthesis and Comparison of the Electronic Spectral Properties of these Linear and Angulnin Triheterocycles Related to $\gamma$Bases", J. Org. Chem. vol. 42, No. 20 (1977), pp. 3292–3296.
Secrist et al., "Fluorescent Modification of Adenosine--Containing Coenzymes, Biological Activities and Spectroscopic Properties", Biochem., vol. 11, No. 19, (1972), pp. 3499–3506.
Bollum, "Terminal Deoxynucleotidyl Transferase", The Enzymes, vol. 10, Ed. Boyer, Academic Press, N.Y. (1974), pp. 145–171.
Bollum, "Terminal Deoxynucleotidyl Transferase: Biological Studies", Advances in Enzymology, vol. 47, Ed. Meister, John Wiley & Sons Inc., (1978) pp. 347–374.
McCaffrey et al., "Terminal Deoxynucleotidyl Transferase Activity in Human Leukemic Cells and in Normal Human Thymocytes", N. Eng. J. Med., vol. 292, No. 15, (1975), pp. 775–780.
Bollum, "Terminal Deoxynucleotidyl Transferase As a Hemotopoietic Cell Marker", J. Am. Soc. Hematol, vol. 54, No. 6 (1979) pp. 1203–1214.

Primary Examiner—Thomas G. Wiseman
Attorney, Agent, or Firm—Pravel, Gambrell, Hewitt, Kirk, Kimball & Dodge

[57] ABSTRACT

Terminal Deoxynucleotidyl Transferase (TdT) may now be quantified in a biological sample without interference from other DNA polymerases normally found therein by utilizing labeled deoxynucleoside triphosphates and/or labeled single stranded oligodeoxynucleotides which have been chemically modified to impair or destroy their ability to form nucleotide base pairs by hydrogen bonding. Such modified deoxynucleoside triphosphates and/or oligodeoxynucleotides of impaired base forming abilities are selectively synthesized by TdT into fluorescently or radioactively labeled acid insoluble polydeoxynucleotides which may be quantified to determine the amount of TdT originally present in the biological sample.

11 Claims, No Drawings

METHOD FOR THE QUANTITATIVE DETERMINATION OF TERMINAL DEOXYNUCLEOTIDYL TRANSFERASE IN BIOLOGICAL SAMPLES

BACKGROUND OF THE INVENTION

Terminal Deoxynucleotidyl Transferase (TdT) is a unique DNA polymerase which in normal tissues is restricted to cell populations of the thymus and bone marrow. Because of its restricted distribution, it has been used as a marker of T-cell differentiation.

Since the discovery of TdT's association with acute lymphoblastic leukemia, there has been an expandind proliferation of reports on the association of TdT and neoplasms of lymphoid origin. TdT has proved to be a useful marker in classifying acute leukemia, malignant lymphoma and the blast phase of chronic granulocytic leukemia. Its presence provides an objective method of classification, obviating the ambiguties often found when relying upon morphological criteria alone. The importance of proper classification (which is synonomous with 'specific diagnosis') is demonstrated by recent observations of acute undifferentiated leukemia and chronic granulocytic leukemia in blast crisis, where the presence of TdT is predictive of initial responsiveness to vincristine and prednisone.

In addition to functioning as an aid in the proper classification of lymphoid neoplasms, TdT serves as a sensitive monitor of remission and relapse. The enzyme disappears from the blood during remission and reappears up to several months before relapse may be detected by the presence of circulating blasts in the peripheral blood, thereby providing an early warning of the need for revised or repeated chemotherapy.

The conventional method to determine TdT activity involves processing of the sample, while the second stage is the testing of the processed sample for enzymatic activity.

It is a general requirement of enzymology that enzymes originating and functioning in cells must be made accessible to substrates in order that enzymatic activity be detected. As the cell membrane is impermeable to most enzymatic substrates, its integrity must somehow be disrupted. This is accomplished by selectively permeabilizing cells (treatment with cold shock or toluene, DEAE-dextran, or trypsin, or isotonic detergent, or hypotonic shock, etc.), by cell fixation (treatment with organic solvents, or aldehydes, etc.), or by cellular disruption (treatment with detergent in high salt concentration, or sonication). The two methods most commonly used for preparing biological samples for detecting cellular TdT are cellular disruption by sonication or detergent with high salt concentration treatment. Both procedures result in a crude extract of solubililized enzymes, proteins, nucleic acids, DNA, and other crude cellular constituents. If testing for TdT is conducted in a non-cellular media, cellular disruption and enzyme solubilization has already been effected by the process of cell death.

At this point, as a crude extract, TdT can be tested directly; however, a large increase in activity occurs with partial purification. Consequently, in order to maximize sensitivity and minimize sample size, partial purification such as by phosphocellulose choromotogrpahy or DEAE-sephadex may be and preferrably is carried out. Fractions are then tested directly for TdT activity.

The second stage of determining levels of TdT is the testing of the processed sample for enzymatic activity. The assay is performed by incubating the sample with fluorescently or radioactively labeled primers and/or substrates under conditions suitable for the enzymatic production of acid insoluble polydeoxynucleotides which, by reason of either the primer or substrate employed, are labeled for subsequent detection and quantification by known methods.

There are a variety of assay systems in use. The two most common are the cacodylate-$Mg^{++}$ system of Bollum and the Tris-$Mn^{++}$ system of McCaffrey. The necessary reagents for analysis are the enzyme sample, DNA primer, deoxynucleoside triphosphate substrate, a divalent metal and a buffer solution.

In a first version of the method, wherein a labeled substrate and unlabeled primer are employed, the primer is a single stranded oligodeoxynucleotide, polydeoxynucleotide or activated denatured DNA. In this version of the method, if TdT is present in the sample, incubation of these reagents in the buffer solution at 35° to 37° C. results in the production of unlabeled DNA primers extended with flourescently or radioactively labeled nucleotide substrates to yield an acid insoluble polydeoxynucleotide. The reaction is stopped by addition of cold trichloroacetic acid (TCA) to a concentration of about 5% by weight. The TCA addition precipitates the polydeoxynucleotide formed by the DNA polymerases present in the sample while the unreacted nucleoside triphopsphate substrates remain in the buffer solution. When radioactively labeled substrates are used the polydeoxynucleotides' precipitate is collected on filter paper discs and its radioactively measured by a liquid scintillation counter. Alternatively, when flourescently labeled substrates are employed the polydeoxynucleotide precipitate is collected, centrifuged, washed with cold 5% TCA, redissolved in water and then measured in a fluorometer.

In a second version of the assay method, wherein labeled primers and unlabeled substrates are used, an oligodeoxynucleotide (usually of less than twenty nucleotides for solubility purposes) is used as the primer and incubation results in the production of a polydeoxynucleotide comprising a labeled primer extended by unlabeled substrates. Addition of cold TCA precipitates the polydeoxynucleotide while the oligodeoxynucleotide remains in the buffer solution. The polydeoxynucleotide is collected as described above and its radioactivity or fluorescence, depending upon which type of labeling was used in the primer, is determined.

Many other methods exist for separating the products of reaction from the primers and substrates of the incubation mixture such as ion-exchange, filter discs, thin layer chromatography or dextan-coated charcoal, but the above described procedures are the most commonly employed. The amount of DNA polymerase originally present in the sample is related to the amount of polydeoxynucleotide formed as a function of the sample, primer and substrate amounts used as well as the time period over which such reagents are incubated. The functional relationship is well known.

Present methods for quantifying TdT in biological samples are not specific to TdT. Such methods also respond to the presence of other DNA polymerases contained in the sample and the amount of polydeoxynucleotide formed during incubation is due to the total amount of DNA polymerase present in the sample. Past efforts to prepare the sample extracts in a manner to separate TdT for assay from other common DNA polymerases, such as DNA polymerases α, β, and γ normally found in such samples, have only been partially successful. Generally, even when the extract is purified by phosphocellulose chromotagraphy or ion-filtration chromotagraphy, substantial quantities of potentially interfering DNA polymerases α, β, and γ co-eluted with TdT. Thus, although partial sample purification by chromatographic methods is desirable to increase TdT activity, maximize assay sensitivity and permits use of minimum sample sizes, it has not provided the answer to quantifying TdT without interference by other DNA polymerases.

Recently, several methods have been developed which purport to be more sensitive and specific to the detection and quantification of TdT in biological samples. See for instance Coleman et al., *Cancer Research,* Vol. 36, pp. 120-127, January 1976; and Mertelsmann et al., *Leukemia Research,* Vol. 2, No. 1, pp. 57-69 (1978). The method reported by Coleman employes a cacodylate buffer which is optional for TdT activity while it inhibits the activity of DNA polymerase α and β. Additionally, when the sample assayed has a sufficiently low enzymatic activity to make the assay results ambiguous, it is reassayed with the addition of 10% ethanol and 10 mM N-ethylmaleimide which acts to completely inhibit TdT activity, thus, distinguishing between the sample activity attributable to DNA polymerase β as opposed to that of TdT. In the method reported by Mertelsmann, enzyme samples are assayed in duplicate, with and without the addition of 100 mM ATP (adenosine triphosphate). ATP specifically inhibits TdT without affecting other cellular DNA polymerases. The difference in enzymatic activity between the duplicate samples is attributable to TdT activity.

Such methods are complicated, time consuming and, by reason of the fact that they measure difference in activity values rather than measuring TdT specifically and directly, are not completely free of ambiguity of results.

More recently, an immunofluorescent method for the detection of TdT has been developed, which provides specificity for TdT. In this method, an antibody is produced in animals immunized to purified TdT. The antibody must also then be purified to avoid non-specific staining. By exposing cells fixed on a microscope slide to the TdT specific antibody, a strong binding occurs between the antibody and immobilized intracellular TdT. Cells with TdT may then be detected in a fluorescent microscope by the method of indirect immunofluorescence. In indirect immunofluorescence the detection of antigen-antibody complexes is accomplished by adding a second, fluorescent tagged antibody that specifically binds to antibodies from the animal used to produce the TdT specific antibody.

The problem with this technique is that even purified antibodies are not homogenous, and their binding affinities will vary from animal to animal, resulting in variable staining and detection of TdT. Also, the production and purification of TdT specific antibodies is technically difficult and expensive.

SUMMARY OF THE INVENTION

The present invention pertains to an improved method for quantifying TdT in the presence of other DNA polymerases in a biological sample by utilizing primers and/or substrates which are specifically incorporated by TdT alone into appropriately labeled acid insoluble polydeoxynucleotides. Primers and substrates which are chemically modified to impair or destroy their ability to form nucleotide base pairs by hydrogen bonding are utilized to achieve reaction specificity for TdT.

DETAILED DESCRIPTION OF THE PREFERRED EMBODIMENTS

With the rare exception of DNA found in some virus classes, native DNA produced by replicative DNA polymerases has a double stranded helix structure. Each DNA strand separately comprises a backbone made up of alternate sugar and phosphate groups joined by a regular 3'-5' phosphate diester linkage. To each sugar group in the backbone is attached a nucleotide base of either the purine type—adenine or guanine—or the pyrimidine type—cytosine or thymine. The base sequence of any given DNA molecule is irregular and is a property of the species from which the DNA originates.

The double helix structure for DNA was first proposed by Watson & Crick and is now well accepted as the correct structure for DNA. The structure for DNA is one wherein the two DNA strands are coiled about a common axis with the sugar-phosphate backbone of each strand to the outside of the coil and the nucleotide bases facing to the inside of the coil with any given nucleotide base of one DNA strand joined by hydrogen bonds to a corresponding and complimentary nucleotide base on the other DNA strand. As essential element of the DNA structure is the feature by which the two DNA strands are held together in a double helix configuration. The two strands are held together by hydrogen bonds formed between nucleotide base pairs which are orientated to the inside of the double helix. The pairing arrangement is very specific and only certain pairs of bases will fit within the internal dimensions required by the double helix structure of DNA. The backbone of each polynucleotide strand is in the form of a regular helix and any two glucosidic bonds (which join sugar and base) which are attached to a bonded pair of bases must always occur at a fixed distance apart due to the regularity of the helix structure of the two backbones to which the bases are joined. Thus, of the base pairs which join by hydrogen bonding of the inside of the double helix structure, one member of the pair must always be a purine type base and the other a pyrimidine in order to properly bridge the two strands. As a direct consequence of the regularity of the phosphate-sugar backbone, only certain specific pairing of bases is permitted by dimensional and geometrical considerations. Thus, adenine pairs with thymine and quanine pairs with cytosine. Such base pairs comply with the necessary geometrical and dimensional restrictions imposed by the double helix structure of DNA.

Cellular DNA polymerases catalyze a template dependent reaction. That is, to synthesize the formation of new DNA strands, DNA polymerase requires the presence of a pre-existing single strand of DNA to utilize as a template by which the DNA polymerase properly directs and orientates incoming deoxynucleoside triphosphate substrates for incorporation into the new DNA strand being formed. The new DNA strand is thereby formed with a base sequence complimentary to that of the template strand and is thus capable of annealing to and forming the double helix structure with the template strand.

Recent evidence also suggests that DNA polymerases are primer dependent, at least to the extent that the presence of a primer strand promotes a much higher degree of DNA synthesis activity by DNA polymerases. When DNA polymerase is primer dependent, as well as template dependent, the primer strand (to which deoxynucleotide substrates are added) must be complimentary to and capable of annealing by hydrogen bonding to its complimentary base sequence in the template strand in order for it to promote DNA synthesis by DNA polymerase.

Terminal Deoxynucleotidyl Transferase, TdT, is a DNA polymerase with the unique property of catalyzing deoxyribonucleotide addition to the 3'-OH terminus of a DNA primer in the absence of any directing template polynucleotide. Thus, unlike all other cellular DNA polymerases which catalyze a template dependent and a primer dependent DNA synthesis reaction, TdT is a primer dependent but template independent DNA polymerase which catalyzes the polymerization of deoxynucleoside triphosphates on to suitable acceptor oligodeoxynucleotides and/or polydeoxynucleotides.

I have now determined that the property of TdT of being template independent and primer dependent may be utilized in a specific assay method for its quantitative determination without interference by other cellular DNA polymerases contained in the sample to be assayed, provided that suitably modified derivatives of single stranded oligodeoxynucleotides and/or deoxynucleoside triphosphates are employed as the primer and/or substrate reagents in the assay procedures heretofore used.

As a consequence of the template independent reaction catalyzed by TdT versus template dependent reactions with other DNA polymerases (such as DNA polymerases $\alpha$, $\beta$ and $\gamma$), deoxynucleoside triphosphate derivatives which have been modified to destroy or impair their ability to form nucleotide base pairs of the dimensions and geometry required by the double helix structure of DNA will be selectively incorporated into higher molecular weight acid insoluble polydeoxynucleotides by TdT alone. Such deoxynucleoside triphosphate derivatives, unable to match with the bases of a template strand because of steric restrictions, will be rejected by template dependent DNA polymerases. Alternatively, since TdT is uniquely primer dependent insofar as it will accept as an initiator single stranded oligodeoxynucleotides, by using as an initiator only those primers whose nucleotide bases have been modified to destroy or impair their ability to form nucleotide base pairs, reaction specificity may be achieved for TdT alone. Such a primer will be suitable for TdT, being incorporated into higher molecular weight acid insoluble polydeoxynucleotides; however, it will be incapable of annealing to complimentary single stranded base sequences in contaminating cellular DNA found in the assay sample and thereby incapable of serving as a primer for template-primer dependent DNA polymerases.

Deoxynucleoside triphosphate derivatives modified to have impaired base pairing abilities (as substrates) or oligodeoxynucleotides modified to have impaired base forming abilities (as primers) may be incubated with crude tissue homogenates, partially purified fractions, permeabilized cells, fixed cells, or serum to specifically detect TdT in such samples without interference with other DNA polymerases. In particular the fluorescent nucleotide, 1,$N^6$-ethenodeoxy-adenosine triphophate and 2-aza-1, $N^6$-ethenodeoxyadenosine triphosphate, or fluorescent oligodeoxynucleotides containing as bases 1,$N^6$-ethenoadenosine or aza-1,$N^6$-ethenoadenosine, will be selectively incorporated into higher molecular weight polydeoxynucleotides by TdT alone which may be detected by virtue of its fluorescence or radioactivity if so labeled.

This method offers substantial improvements in the technology of measuring TdT activity because of its strict specificity for TdT. Current methods do not allow for sufficient discrimination between polymerization of polydeoxynucleotides by TdT versus a terminal addition reaction of the templte dependent DNA polymerases.

Since the essential attribute of the DNA double helix is that the regularity of the sugar-phosphate ester backbone imposes a restriction on the base pair formation, this necessitates that any base pair must be constrained by geometric conditions to a length of approximately 11 Å (measured from the point of origin of the base on its respective sugar to the corresponding point of its complimentary base on the opposite chain). As the function of replicative DNA polymerases is to duplicate DNA, only those base pairs containing regions of identical dimensions and geometry will be recognized and incorporated into a growing DNA chain by template dependent DNA polymerases. Secondly, for the purpose of DNA polymerases, the incoming base of the growing chain must be able to form hydrogen bonds with the directing base of a template DNA strand. If the directing base of the template is unable to form hydrogen bonds with the incoming base, then template dependent DNA polymerases will reject that incoming base and it will not be incorporated into the new DNA strand being formed.

Substrates and primers may be modified to render them incapable of utilization by DNA polymerases other than TdT by chemically modifying those positions of their nucleotide bases which are involed in hydrogen bonding. The addition of substituent groups which possess sufficient steric bulk to the hydrogen bonding sites of such bases preclude the modified base from approaching an unmodified base to within the 11 Å distance required by the double helix structure of DNA and effectively renders such modified bases incapable of hydrogen bonding—hence incapable of forming a base pair. Alternatively, the substrate or primer may be rendered incapable of forming base pairs by the incorporation of non-hydrogen bonding substituents at its hydrogen bonding sites.

In the case of the adenine-thymine base pair (with the hydrogen bonding represented by broken lines):

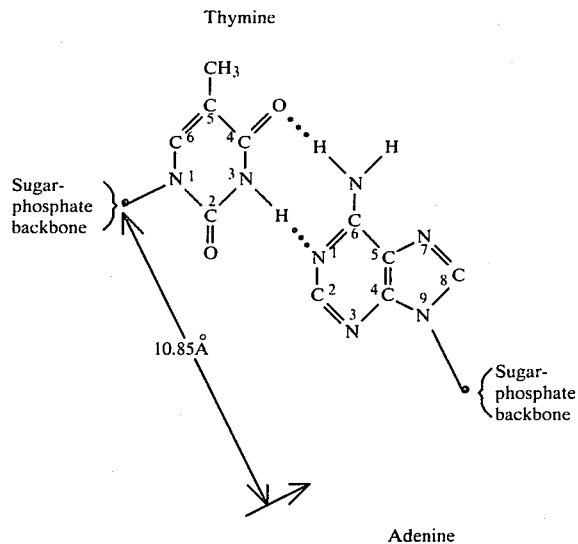

Thymine ··· Adenine

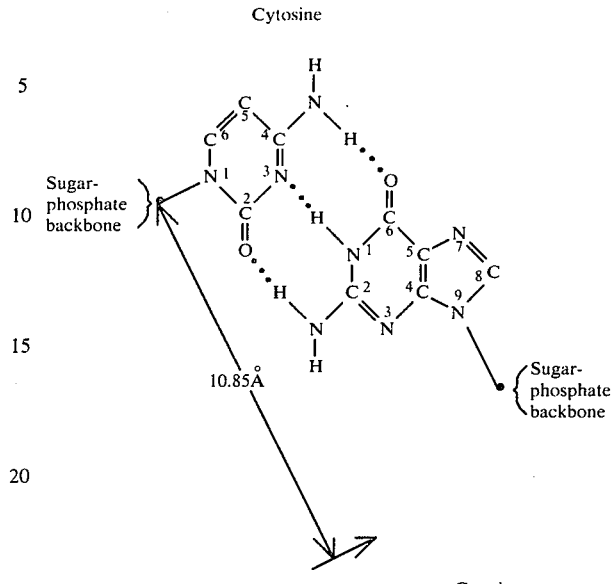

Cytosine ··· Guanine assuming that adenine is the directing base of the template DNA strand, a thymine analogue with a non-hydrogen bonding substitution at or in place of the 4-keto position or a non-hydrogen bonding substitution at the 3-amino position will result in loss of a single hydrogen bond (leaving only one hydrogen bond at the reciprocal position), and thereby result in impaired base pairing ability. Substitutions involving both positions result in no sites capable of hydrogen bond formation and therefor absent base pairing ability.

If the template directing base is thymine, then adenine analogues with non-hydrogen bonding substitution at or in place of the 6-amino position or a non-hydrogen bonding substitution at the 1-N position will result in the loss of a single hydrogen bond (leaving only one hydrogen bond at the reciprocal position), thereby resulting in impaired base pairing ability. Substitutions at both positions result in no sites capable of hydrogen bond formation and therefor absent base pairing ability.

An important criteria which must be met in order that substitutions of the base analogues result in loss of hydrogen bonding ability is that the substituent group not be capable of rotating away from the plane of base pairing. As an example, 6-methylaminoadenosine triphosphate is a substrate for the replicative RNA polymerases. It retains its capability for hydrogen bonding—hence base pairing—because the methyl group may rotate out of the hydrogen bonding axis, allowing the remaining 6-amino hydrogen to form oridinary hydrogen bonds and thereby retain base pairing ability. However, 6-dimethylaminoadenosine triphosphate will not function as a substrate for the replicative RNA polymerases. In the case of the dimethyl substitution there is no remaining 6-amino hydrogen which can rotate into the plane of base pairing and form hydrogen bonds. Therefore, 6-dimethylaminoadenine has impaired base pairing ability. But 6-dimethylaminoadenine remains a substrate for a template independent RNA polymerase, polynucleotide phophorylase; an enzyme analogous to TdT.

In the case of the cytosine-guanine base pair (hydrogen bonding represented by broken lines):

if cytosine is the template directing base, then guanine analogues formed with a non-hydrogen bonding substitution at or in place of the 2-amino, 6-keto or 1-imino position will have the loss of a single hydrogen bond (leaving only two hydrogen bonding sites) and thereby have impaired base pairing abilities. Substitutions at two of the hydrogen bonding sites will result in even greater impairment in base pairing. Substitutions at all three hydrogen bonding sites result in absent base pairing ability.

If guanine is the template directing base, then cytosine analogues formed with a non-hydrogen bonding substitution at or in place of the 2-keto position, or a non-hydrogen bonding substitution at or in place of the 4-amino position, or a non-hydrogen bonding substitution in place of the 3-N will have impaired base pairing abilities. Substitutions at two of these hydrogen bonding positions will result in an even greater impairment in base pairing ability of such analogues. Substitutions at all three positions will result in absent base pairing ability.

The adenine base of deoxyadenosine triphosphate (dATP) substrates or oligodeoxyadenosine primers may be modified in several ways to impair its base pairing ability. The 6-amino position may be doubly alkylated by reaction with an alkyl halide wherein the alkyl group ranges from one to three in carbon number, thus rendering it incapable of hydrogen bonding at this position. Additionally, the 6-dialkylaminoadenosine triphosphate, since its steric bulk at the 6 position is increased, is incapable of approaching to within the required 11 Å base pair distance of 4-keto position of a thymine base to which it would otherwise pair. This effectively prevents the approach of the modified dATP at its 1-N position to within the required distance of the 3-N position of a thymine to provide for the required base pair distance of 11 Å, thus impairing the ability of the modified dATP to form hydrogen bonds at its 1-N position.

Preferably, dATP or oligo (dA) is modified by converting the adenine bases thereof into etheno-adenine derivatives, such as in 1, $N^6$-ethenoadenosine.

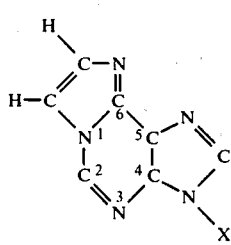

1,N⁶-ethenoadenosine
X = sugar-phosphate backbone
or triphosphate

As the 6-amino and the 1-N positions of adenine are solely responsible for hydrogen bonds in its base pairing with thymine, its modification to contain an etheno bridge between these positions destroys its base pairing capabilities. The etheno bridge destroys the required functionality for hydrogen bond formation (i.e. hydrogen on the 6-amino group and an electronegative ring nitrogen at 1-N) and by virtue of steric restrictions increases the minimal approaching distance between the so modified adenosine to a thymine base beyond the required 11 Å.

Likewise the adenosine may be converted to 1, N⁶-etheno-2-aza-adenosine:

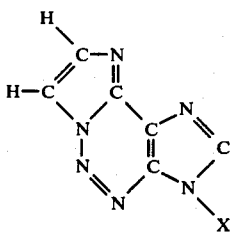

1,N⁶-etheno-2-aza-adenosine
X = sugar-phosphate backbone
or triphosphate which is incapable of base pairing by hydrogen bonding with thymine for the reasons discussed above concerning 1,N⁶-etheno-adenosine.

Where the nucleotide bases of the primer or substrates comprise cytosine, they may be modified to render them incapable of hydrogen bonding by reaction with chloroacetaldehyde to form an etheno bridge across the N⁴ amino and 3-N position to form 3,N⁴-ethenocytosine:

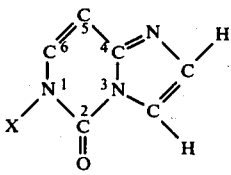

4,N³-ethenocytosine
X = sugar-phosphate backbone
or triphosphate

The etheno bridge disrupts two of the three possible hydrogen bonding sites and increases the minimum approaching distance to its base pair, guanine, as to effectively prevent a hydrogen bond from forming at cytosine's 2-keto position.

Where the nucleotide bases of the primer or substrates comprise guanine, they may be modified to render them incapable of hydrogen bonding by reaction with chloracetaldehyde to form an etheno bridge across the N² amino and 1-N position to form 1,N²-etheno-guanine:

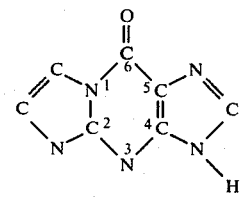

1,N²-ethenoguanine
X = sugar-phosphate backbone
or triphosphate

The etheno bridge disrupts two of the three possible hydrogen bonding sites and increases the minimum approaching distance to its base pair, cytosine, as to effectively prevent a hydrogen bond from forming at guanine's 6-keto position.

1,N²-ethenodeoxyguanine compounds can be synthesized by the method of Sattsangi et al, in *J. Org. Chem.*, Vol. 42, No. 20, P. 3292 (1977).

Etheno derivatives of adenosine compounds can be synthesized from compounds containing adenine, such as deoxyadenosine monophosphate or oligodeoxyadenylic acid, which are commercially available, by the method of Secrist and Barrio, "Fluorescent modification of adenosine containing coenzymes"; *Biochemistry*, 11 (19), p. 3499 (1972). Briefly, this consists of reacting the adenosine containing compounds with about 1M chloracetaldehyde at room temperature and pH 4 to 6 for several days until the reaction has progressed to quantitative completion. Purification can be accomplished by ethanol precipitation or ion-exchange chromatography.

The 2-aza-etheno-adenosine compounds can be synthesized by the method of Tsou and Yip, "Synthesis of aza-ethenoadenosine: a new cytotoxic fluorescent nucleoside," *Nucleic Acids Research* 1(4): 531, (1974).

Specific derivatives of deoxynucleoside monophosphates are synthesized and then phosphorylated, forming deoxynucleoside triphosphates, which are substrates for TdT. This approach is preferable to derivatizing the parent deoxynucleoside triphosphates directly because of the marked lability of the phosphate groups under synthetic reaction conditions.

Deoxynucleoside monophosphates may be conveniently converted to the triphosphate form by the method of Hoard and Ott, "Conversion of mono and oligodeoxyribonucleotides to 5'-triphosphates," *J. American Chemical Society*, 87(8), 1785, (1965). Briefly, this method consists of the reaction of the phosphorimadazolidate formed from a nucleoside monophosphate and 1,1'-carbonylidiimidazole with inorganic pyrophosphate, yielding the nucleoside triphosphate in good yield. The resulting nucleoside triphosphate can be purified by chromatography on an ion-exchange column, such as DEAE-cellulose.

The methods for synthesizing oligodeoxynucleotide etheno or aza etheno derivatives is essentially the same as for deoxynucleoside monophosphates. Synthesis of base modified oligodeoxynucleotides can be accomplished by directly derivatizing the parent compound.

As stated earlier, the two methods for improved determination of TdT activity involve either nucleotides or oligonucleotides with impaired base pair forming ability. Nucleotides offer the advantage of lower cost than oligonucleotides, but have decreased stability.

In radiochemical determinations, labeled etheno-dATP (or oligo etheno-dA), aza-etheno-dATP (or oligo aza-etheno-dA), etheno-dGTP (or oligo etheno-dG), or dialkyl-dATP (or oligo dialkyl-dA) may be used to specifically and sensitively detect TdT. Derivatives of cytosine or thymidine with impaired base pair forming abilities will have substantially reduced activity compared to adenine or guanine deriatives. This is because the parent compounds with the bases cytosine and thymine are incorporated into polydeoxynucleotides at a markedly slower rate than the corresponding adenine or guanine compounds. Therefore, though of comparable specificity, derivatives of cytosine and thymine will not permit optimal sensitivity for assaying TdT.

In fluorescent determinations, etheno-dATP (or oligo etheno-dA), or aza-etheno-dATP (or oligo aza-etheno-dA) are the reagents of choice for specifically and sensitively detecting TdT. Although etheno-dCTP is fluorescent, when incorporated into DNA its fluorescence is lost. Consequently, it is not suitable for fluorescent methods. Also, the same applies to etheno-dGTP, as these compounds are not fluorescent.

If determining incorporation of fluorescent nucleotides (or oligodeoxynucleotides) into polydeoxynucleotides in situ; that is, in fixed or permeabilized cells (i.e. a histochemical method), then only aza-etheno-dATP (or oligo aza-etheno-dA) is suitable. This is because it has a fluorescent emission spectrum at longer wavelengths than etheno-dATP (or oligo etheno-dA), which will not be obscured by the intrinsic autofluorescence of tissue and cells. In the histochemical method, incubation of fixed or permeabilized cells in a reaction mixture containing aza-etheno-dATP (or oligo aza-etheno-dA), buffer, divalent metal cation, and primer (or nucleotides) results in the enzymatic synthesis in situ of fluorescent polydeoxynucleotide. Those cells containing TdT will be visibly stained a fluorescent green when viewed under a fluorescent microscope, after washing off the unused TCA soluble reaction substrates.

The in situ detection of TdT in fixed or permeabilized cells offers advantages over the immunofluorescent method. The fluorescent substrates and primer are well defined chemicals which may be prepared simply and in bulk. Unlike antibodies, they are homogenous and without variability from batch to batch. Also, the histochemical method specifically detects an enzymatic reaction, rather than an antigen. The immunofluorescent method would detect antigenic, enzymatically inactive precursors or degradation products of TdT. This would be important if the enzymatic function of TdT is related to the pathogenesis of leukemias and lymphomas.

To illustrate that suitable modified deoxynucleoside triphosphates and/or single stranded oligodeoxynucleotides which have impaired basing pairing abilities, as described above, are specific to TdT, tritium labeled ethenodeoxyadenosine triphosphate (etheno dATP) and tritium labeled deoxyadenosine triphosphate (dATP) were appropriately incubated with a purified TdT enzyme sample and with a purified $E.$ $coli$ DNA polymerase I sample. The test on enzyme activity of the TdT sample showed progressive incorporation of both etheno-dATP and dATP into acid insoluble polydeoxynucleotides over the 90 minute incubation period. However, test on the enzyme activity of the $E.$ $coli$ DNA polymerase I (a replicative template primer dependent enzyme) sample showed no detectable incorporation of etheno-dATP over a 90 minute incubation period, while showing that dATP was normally and appreciably incorporated into an acid insoluble polydeoxynucleotide over the same period of time.

The following illustrates the manner in which the TdT detection technique of the invention may be applied to histochemical and radiochemical TdT detection methods.

IMPROVED HISTOCHEMICAL METHOD

Blood from a patient is collected into anticoagulated tubes. A blood smear is made upon a microscope slide and immediately fixed in cold methanol or glutaraldehyde for several minutes. The microscope slide is washed with cold, 50 mM phosphate buffer, at pH 7, for several minutes. The slide is then immersed in a solution containing:

200 mM cacodylate, potassium salt, pH 7.4
4 mM magnesium chloride;
2 mM mercaptoethanol
2 micrograms/ml $p(dA)_{10}$
1 mM aza-etheno-dATP and incubated in the reaction solution for about 15 minutes at an optimal temperature of 37° C. The slide is then washed in cold 95% ethanol, and then washed for several minutes in ice cold 5% trichloroacetic acid (TCA). Finally, the slide is washed in cold 95% ethanol, dried and mounted with a cover slip. The slide is examined under a fluorescent microscope, utilizing an exciting light with a peak wavelength near 360 millimicrons and appropriate filters to detect fluorescence at approximately 500 millimicrons. Cells with TdT will be seen to fluoresce a green color; whereas, cells lacking TdT will not be stained.

IMPROVED RADIOCHEMICAL METHOD

Blood from a patient is collected into anticoagulated tubes. The blood is added to Ficoll-Hypague and the white cells are separated by standard technique of centrifugation at 4° C. The white cells are aspirated from the interface and washed once in phosphate buffered saline. The cells are suspended at a concentration of $1-5 \times 10^7$ cells/ml in 0.15 M KCL, 50 mM Tris-HCL pH 7.8, 0.1 mM K-EDTA, 10% glycerol, 10 mM dithiotreitol, 1 mg/ml bovine serum albumin, 0.5% Triton-X-100, 5 mM phenylmethylsulfonyl fluoride. Cells are disrupted by sonication. The homogenate resulting from sonication is applied to a DEAE-Sephadex column (0.6×20 cm) equilibrated with 50 mM KCL, 50 mM Tris-HCL pH 7.8, 0.1 mM EDTA, 20% glycerol, and 10 mM dithitreitol. One milliliter fractions are collected as the column is eluted with 0.5 M KCL, 50 mM Tris pH 7.8, 20% glycerol, 0.1 mM EDTA, 10 mM dithiotreitol buffer. Aliquots of 25 microliters from each fraction are assayed for TdT activity in 75 microliters of the following reaction mixture:

50 mM Tris pH 7.8, 1 mM dithiotreitol, 50 mM KCL,
10 mg bovine serum albumin, 0.6 mM $MnCl_2$,
0.5 micrograms oligo $(dA)_{12-18}$, and
50 micromolar tritium labeled ethenodeoxyadenosine triphosphate The reaction mixture is incubated for 1 hour at 37° C. The reaction is stipped by the addition of 2.5% trichloroacetic acid, 4 mM sodium pyrophosphate. Precipitated nucleic acids are collected by filtration on Whatman GFB filter discs, and washed with cold 5% TCA and cold 95% ethanol. The filter discs are then placed in a liquid scintillator, and radioactivity quantitated in a liquid scintillation counter. The amount of tritium label etheno-dATP incorporated into TCA insoluble DNA is a measure of the amount of TdT present in the sample.

Although the invention has been described with reference to its preferred embodiments, those of ordinary skill in the art may make modifications or changes thereto without departing from the scope and spirit of the invention as described above claimed hereafter.

I claim:

1. A method for quantifying Terminal Deoxynucleotidyl Transferase (TdT) in a biological sample containing solubilized DNA polymerases, by incubating at from about 35 to about 37° C. a buffered mixture of said sample with oligodeoxynucleotide primers and deoxynucleotide substrates, wherein the primer or the substrate is labeled for detection, in the presence of a divalent metal to produce by DNA synthesis labeled acid insoluble polydeoxynucleotides which are insoluble from said incubation mixture and from the quantification of which the amount of TdT in the extract is determinable, wherein the improvement comprises:

incubating said enzyme sample with labeled oligodeoxynucleotide primers or labeled deoxynucleotide substrates sufficiently chemically modified at one or more of the base moieties of said primers or substrates by one or more nonhydrogen bonding or bulky substituents groups to impair or destroy the ability of such primers or substrates to form nucleoside base pairs by hydrogen bonding, thereby permitting direct quantification of TdT in the sample without interference by other DNA polymerases present in the sample by rendering such primers or substrates selective to utilization by TdT in the synthesis of labeled polydeoxynucleotides.

2. The improvement of claim 1 wherein the chemically modified deoxynucleotide substrate in $1,N^6$-ethenodeoxyadenosine triphosphate.

3. The improvement of claim 1, wherein the chemically modified deoxynucleotide substrate is $1,N^6$-etheno-2-aza-deoxyadenosine triphosphate.

4. The improvement of claim 1 wherein the chemically modified deoxynucleotide substrate is a 6-dialkylamino-deoxyadenosine triphosphate wherein the alkyl groups each independently has from one to about three carbon atoms.

5. The improvement of claim 1 wherein the chemically modified deoxynucleotide substrate is $3,N^4$-ethenodeoxy-cytosine triphosphate.

6. The improvement of claim 1, wherein the chemically modified deoxynucleotide substrate is $1,N^2$-etheno-deoxyquanosine triphosphate.

7. The improvement of claim 1, wherein the oligodeoxynucleotide primer is a buffer solution soluble oligo-2-aza $1,N^6$-ethenodeoxyadenosine.

8. The improvement of claim 1, wherein the oligodeoxynucleotide primer is a buffer solution soluble oligo-$1,N^2$-etheno-deoxyquanosine.

9. The improvement of claim 1, wherein the oligodeoxynucleotide primer is a buffer solution soluble oligo-6-dialkylaminodeoxyadenosine.

10. The improvement of claim 1, wherein the oligodeoxynucleotide primer is a buffer solution soluble oligo-$1,N^6$-ethenodeoxyadenosine.

11. The improvement of claim 1 wherein the oligodeoxynucleotide primer is a buffer solution soluble oligo-$3,N^4$-ethenodeoxycytosine.

* * * * *